(12) United States Patent
Messina et al.

(10) Patent No.: US 12,274,461 B2
(45) Date of Patent: Apr. 15, 2025

(54) ADJUSTABLE INTERFACE DEVICE FOR CONNECTING COMPONENTS OF A MEDICAL DEVICE

(71) Applicant: Bard Peripheral Vascular, Inc., Franklin Lakes, NJ (US)

(72) Inventors: Genevieve Messina, Mesa, AZ (US); Alexander Palmer, Scottsdale, AZ (US)

(73) Assignee: Bard Peripheral Vascular, Inc., Franklin Lakes, NJ (US)

(*) Notice: Subject to any disclaimer, the term of this patent is extended or adjusted under 35 U.S.C. 154(b) by 462 days.

(21) Appl. No.: 17/761,636

(22) PCT Filed: Sep. 25, 2019

(86) PCT No.: PCT/US2019/052936
§ 371 (c)(1),
(2) Date: Mar. 18, 2022

(87) PCT Pub. No.: WO2021/061119
PCT Pub. Date: Apr. 1, 2021

(65) Prior Publication Data
US 2022/0330963 A1    Oct. 20, 2022

(51) Int. Cl.
*A61B 17/22* (2006.01)
*A61B 17/00* (2006.01)

(52) U.S. Cl.
CPC ............ *A61B 17/22012* (2013.01); *A61B 2017/00477* (2013.01); *A61B 2017/22018* (2013.01)

(58) Field of Classification Search
CPC .... A61B 17/22012; A61B 2017/00477; A61B 2017/22018; A61B 2017/22014;
(Continued)

(56) References Cited

U.S. PATENT DOCUMENTS 5,423,846 A    6/1995  Fischell
5,466,222 A    11/1995 Ressemann et al.
(Continued)

FOREIGN PATENT DOCUMENTS

JP    2012533346 A    12/2012
JP    2014057746 A  *  4/2014
(Continued)

OTHER PUBLICATIONS

Office Action dated Jul. 14, 2023 pertaining to Japanese application 2022-518715.
(Continued)

*Primary Examiner* — Tan-Uyen T Ho
*Assistant Examiner* — Cherie M Poland
(74) *Attorney, Agent, or Firm* — Dinsmore & Shohl LLP (57) ABSTRACT

An adjustable interface device for connecting two components of a medical device includes an elongate body and an elongate member. The elongate body has a first end, a second end, an interior channel, and a side wall that surrounds the interior channel. The side wall defines a first connector portion adjacent the second end. The first connector portion attaches to a respective one of the components of the medical device. The elongate member has a head end portion and a shaft portion that longitudinally extends from the head end portion. The shaft portion is located at least partially in the interior channel of the elongate body. The shaft portion is configured to slidably move axially along the longitudinal axis to adjust a length of the adjustable interface device. The head end portion defines a second connector portion that attaches to another of the components of the medical device.

21 Claims, 6 Drawing Sheets

(58) Field of Classification Search
CPC ...... A61B 2090/061; A61B 2090/0807; A61B 2090/0811
See application file for complete search history.

(56) References Cited

U.S. PATENT DOCUMENTS

| | | | |
|---|---|---|---|
| 6,613,017 | B1 | 9/2003 | Mickley |
| 6,991,596 | B2 | 1/2006 | Whalen et al. |
| 8,147,480 | B2 | 4/2012 | Hoofnagle et al. |
| 8,454,579 | B2 * | 6/2013 | Fangrow, Jr. ...... A61M 39/1011 |
| | | | 604/539 |
| 8,715,240 | B2 | 5/2014 | Cunningham |
| 8,728,058 | B2 | 5/2014 | Schertiger |
| 9,517,324 | B2 | 12/2016 | Deshpande |
| 9,821,141 | B2 | 11/2017 | Stice et al. |
| 2004/0143240 | A1 | 7/2004 | Armstrong et al. |
| 2009/0088730 | A1 | 4/2009 | Hoofnagle et al. |
| 2010/0249723 | A1 * | 9/2010 | Fangrow, Jr. ......... A61M 39/02 |
| | | | 604/247 |
| 2014/0018732 | A1 * | 1/2014 | Bagaoisan ........ A61M 25/0136 |
| | | | 604/95.04 |
| 2014/0228874 | A1 | 8/2014 | Boyd et al. |
| 2016/0008571 | A1 | 1/2016 | Boyle et al. |
| 2016/0263329 | A1 * | 9/2016 | Young ............... A61M 5/31528 |
| 2017/0000990 | A1 | 1/2017 | Gerrans et al. |
| 2017/0252536 | A1 | 9/2017 | Yang et al. |
| 2018/0055529 | A1 * | 3/2018 | Messerly ............... H10N 30/50 |
| 2018/0289393 | A1 * | 10/2018 | Bankiewicz ....... A61B 17/3478 |

FOREIGN PATENT DOCUMENTS

| | | | | |
|---|---|---|---|---|
| WO | WO 8300622 A1 * | 3/1983 | ............... | A61J 7/00 |
| WO | 2012096816 A1 | 7/2012 | | |

OTHER PUBLICATIONS

Notice of Allowance dated Dec. 26, 2023 pertaining to JP 2022-518715 filed Mar. 23, 2022.

* cited by examiner

ADJUSTABLE INTERFACE DEVICE FOR CONNECTING COMPONENTS OF A MEDICAL DEVICE

CROSS-REFERENCE TO RELATED APPLICATIONS

This application is a U.S. National Phase of International Application No. PCT/US2019/052936, entitled "ADJUSTABLE INTERFACE DEVICE FOR CONNECTING COMPONENTS OF A MEDICAL DEVICE" and filed Sep. 25, 2019, which is incorporated herein by reference in its entirety.

TECHNICAL FIELD

The present invention relates to a medical device, and, more particularly, to an adjustable interface device for connecting components of a medical device.

BACKGROUND ART

Medical devices may be used to perform surgical procedures, such as for example, a vascular occlusion crossing procedure or an atherectomy procedure, so as to restore patency and blood flow that was lost due to one or more intravascular occlusions. One type of medical device is an ultrasonic device configured to perform the vascular occlusion crossing procedure and/or the atherectomy procedure. A crossing procedure is a procedure in which an opening is formed through the intravascular occlusion. An atherectomy procedure may include crossing, but also attempts to break up and remove the intravascular occlusion. The ultrasonic device may include an ultrasonic catheter and a support catheter for performing the procedures.

What is needed in the art is an adjustable interface device that may be interposed between, and connected to, two components of a medical device, wherein the adjustable interface device has an adjustable length.

SUMMARY OF INVENTION

The present invention provides an adjustable interface device that may be interposed between, and connected to, two components of a medical device, wherein the adjustable interface device has an adjustable length.

The invention, in one form, is directed to an adjustable interface device for connecting two components of a medical device. The adjustable interface device includes an elongate body and an elongate member. The elongate body has a first end, a second end, an interior channel, and a side wall that surrounds the interior channel. The interior channel is configured to extend between the first end and the second end. The elongate body has a longitudinal axis that longitudinally extends through the interior channel. The side wall is configured to define a first connector portion adjacent the second end. The first connector portion is configured to attach to a respective one of the two components of the medical device. The elongate member has a head end portion and a shaft portion that longitudinally extends from the head end portion. The shaft portion is located at least partially in the interior channel of the elongate body. The shaft portion is configured to slidably move axially along the longitudinal axis to adjust a length of the adjustable interface device. The head end portion defines a second connector portion configured to attach to the other of the two components of the medical device.

The invention in another form is directed to an ultrasonic device that includes a handpiece, a support catheter and an adjustable interface device. The handpiece includes a handpiece housing, and an ultrasonic catheter connected to the handpiece housing. The handpiece housing is configured with an outer shape and size to facilitate being grasped by an operator. The ultrasonic catheter has a first mounting portion. The support catheter has a catheter body and a catheter sheath connected to the catheter body. The catheter body has a second mounting portion. The catheter sheath has a distal end. The adjustable interface device includes an elongate body and an elongate member. The elongate body has a first end, a second end, an interior channel, and a side wall that surrounds the interior channel. The interior channel is configured to extend between the first end and the second end. The elongate body has a longitudinal axis that longitudinally extends through the interior channel. The side wall is configured to define a first connector portion adjacent the second end. The first connector portion is configured to attach to a respective one of the first mounting portion of the ultrasonic catheter and the second mounting portion of the support catheter. The elongate member has a head end portion and a shaft portion that longitudinally extends from the head end portion. The shaft portion is located at least partially in the interior channel of the elongate body. The shaft portion is configured to slidably move axially along the longitudinal axis to adjust a length of the adjustable interface device. The head end portion defines a second connector portion that is configured to attach to the other of the first mounting portion of the ultrasonic catheter and the second mounting portion of the support catheter.

An advantage of the present invention is that the adjustable interface device may be used, for example, to selectively and easily adapt the ultrasonic device for use in each of a crossing procedure and an atherectomy procedure.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
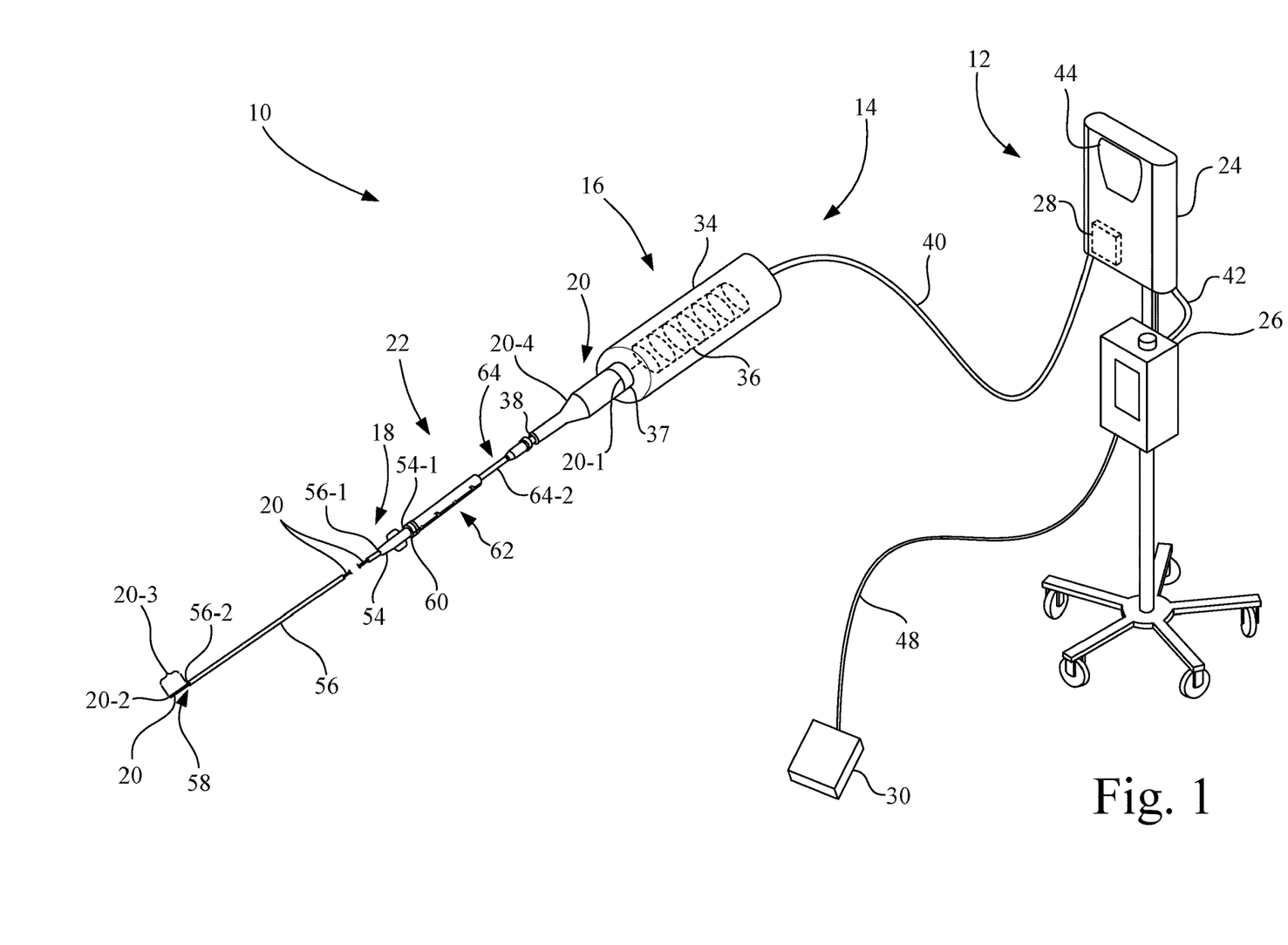
FIG. 1 is a pictorial representation of a medical system that includes an ultrasonic device having an adjustable interface device that is interposed between a handpiece and a support catheter, in accordance with an aspect of the present invention.

Referring now to the drawings, and more particularly to FIG. 1, there is shown a medical system 10 in accordance with an embodiment of the present invention, which may be used for performing a medical procedure, such as an occlusion crossing and/or an atherectomy procedure.

Figure 2:
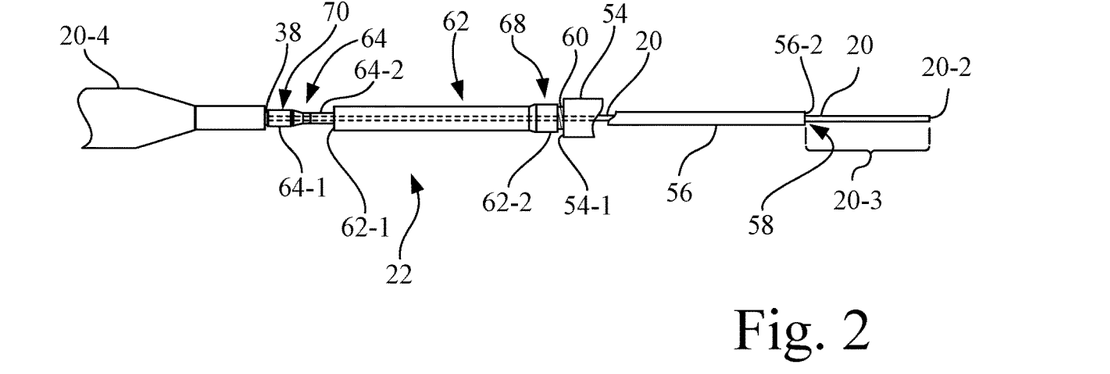
FIG. 2 is an enlargement of a portion of the ultrasonic device of FIG. 1.

In the present embodiment, for example, medical system 10 may include a console 12 and a medical device, such as for example, an ultrasonic device 14. Referring also to FIG. 2, ultrasonic device 14 includes a handpiece 16, a support catheter 18, and an ultrasonic catheter 20. Support catheter 18 is detachably attached to handpiece 16 by an adjustable interface device 22, in accordance with an aspect of the present invention.

In the present embodiment, as depicted in FIG. 1, console 12 includes a user interface 24, a controller 26, and an ultrasonic energy source 28 located in user interface 24. Console 12 may include multiple components in separate housing units, as in the embodiment shown, or may include the multiple components in a single housing unit. Optionally, console 12 also may include a foot switch 30.

In the present embodiment, handpiece 16 includes a handpiece housing 34 and an ultrasonic transducer 36 mounted internally to handpiece housing 34. Ultrasonic catheter 20 is mechanically connected to ultrasonic transducer 36, and to handpiece housing 34. Handpiece housing 34 has an outer shape and size to facilitate being grasped by an operator during a crossing or atherectomy procedure. Handpiece housing 34 includes at its distal end a mounting portion 37 configured to facilitate connection to ultrasonic catheter 20.

Ultrasonic transducer 36 may be, for example, a piezoelectric-type transducer. Ultrasonic transducer 36 of handpiece 16 is electrically connected to ultrasonic energy source 28 by an electrical cable 40. Ultrasonic transducer 36 is configured to receive and convert the ultrasonic electrical excitation signals generated by ultrasonic energy source 28 into ultrasonic vibrational energy, which may be in a frequency range corresponding to that of the ultrasonic electrical excitation signal generated by ultrasonic energy source 28.

User interface 24 of console 12 is connected to controller 26 via an electrical cable 42, e.g., a multi-wire cable or USB, to provide electrical and communication interconnection. Alternatively, user interface 24 may be a wireless link, e.g., Bluetooth, which is communicatively coupled to controller 26. User interface 24 may include, for example, a touchscreen display 44 and associated input and output processing circuitry. Touchscreen display 44 may include, for example, a liquid crystal display (LCD) or a light-emitting diode (LED) display. Alternatively, user interface 24 may be in the form of a laptop computer or tablet. User interface 24 is configured to generate control signals based on user input received by touchscreen display 44. For example, a user may operate touchscreen display 44 of user interface 24 to provide the control signals to controller 26 to initiate and/or terminate operation of ultrasonic energy source 28.

Controller 26 is electrically connected and communicatively coupled to each of user interface 24 and ultrasonic energy source 28. Controller 26 may include, for example, processor circuitry, interface circuitry, and electronic memory circuitry. Controller 26 is configured, for example, to execute program instructions to process signals received from touchscreen display 44 of user interface 24, and to execute program instructions to provide output control signals to ultrasonic energy source 28 to control the operation of ultrasonic energy source 28, such as for example, to control the frequency and/or electrical output power, of the ultrasonic electrical excitation signal generated by ultrasonic energy source 28.

Ultrasonic energy source 28 is connected to ultrasonic transducer 36 via an electrical cable 40. Ultrasonic energy source 28 generates the ultrasonic electrical excitation signal that is delivered to ultrasonic transducer 36. The frequency of the ultrasonic electrical excitation signal may be selectable, and or variable, in a range of 20 kHz to 40 kHz, for example. In some applications, for example, the ultrasonic frequency of the ultrasonic electrical excitation signal may be, or may initially be, at a frequency of 20 kHz.

Foot switch 30 is connected to controller 26 via an electrical cable 48. Foot switch 30 may provide auxiliary input signals to controller 26, which in turn controller 26 may use to activate and deactivate system components, e.g., ultrasonic energy source 28 of medical system 10.

Referring to FIGS. 1 and 2, support catheter 18 includes a catheter body 54, a catheter sheath 56, and a catheter lumen 58. Catheter sheath 56 is connected to catheter body 54. Catheter lumen 58 extends through an entirety of catheter body 54 and catheter sheath 56. In the present embodiment, catheter body 54 and catheter sheath 56 may be formed as an integral unit, wherein a proximal end 56-1 catheter sheath 56 is permanently connected to catheter body 54.

Catheter body 54 has a proximal end 54-1 that defines a proximal end of support catheter 18. Catheter body 54 also includes, at proximal end 54-1, a mounting portion 60 to facilitate connection to adjustable interface device 22.

Catheter sheath 56 of support catheter 18 may be in the form of an elongate flexible tube, such as a polymer tube. Catheter sheath 56 of support catheter 18 includes proximal end 56-1 and a distal end 56-2, and includes a portion of catheter lumen 58. Distal end 56-2 of catheter sheath 56 defines a distal end of support catheter 18. In the present embodiment, catheter lumen 58 is an elongate lumen that longitudinally extends through both of catheter body 54 and catheter sheath 56, to distal end 56-2 of catheter sheath 56, and may be formed as a central lumen, relative to the diameter, of catheter sheath 56.

In the present embodiment, ultrasonic catheter 20 is an elongate member that includes a sheath that surrounds a flexible metal wire, e.g., nitinol. The sheath of ultrasonic catheter 20 is located in, and longitudinally extends within, catheter lumen 58 of catheter sheath 56 of support catheter 18. In the present embodiment, ultrasonic catheter 20 may have a length greater than 60 centimeters (cm), and in some embodiments, for example, a length of 100 cm to 200 cm. Ultrasonic catheter 20 has a proximal end 20-1, a distal tip 20-2, a distal end portion 20-3, and a handpiece 20-4, wherein the sheath of ultrasonic catheter 20 longitudinally extends from handpiece 20-4.

Proximal end 20-1 of ultrasonic catheter 20 is operably connected to ultrasonic transducer 36, e.g., by a sonic connector, to receive the vibrational energy from ultrasonic transducer 36 so as to produce a vibrational motion of at least distal tip 20-2 of ultrasonic catheter 20. The vibrational motion of ultrasonic catheter 20 may be longitudinal or a combination of longitudinal and transverse vibration.

Distal tip 20-2 of ultrasonic catheter 20 may be, for example, a blunt tip, e.g., a rounded tip, that is not pointed. In practice, catheter sheath 56 of support catheter 18 and ultrasonic catheter 20 are advanced into a blood vessel of the vasculature having a vascular occlusion, wherein distal tip 20-2 of ultrasonic catheter 20 engages the vascular occlusion.

Distal end portion 20-3 is the portion of ultrasonic catheter 20 that extends proximally from distal tip 20-2 of ultrasonic catheter 20, and distal end portion 20-3 distally terminates at distal tip 20-2.

Handpiece 20-4 of ultrasonic catheter 20 includes a mounting portion 38 to facilitate connection to adjustable interface device 22.

Figures 3, 4:
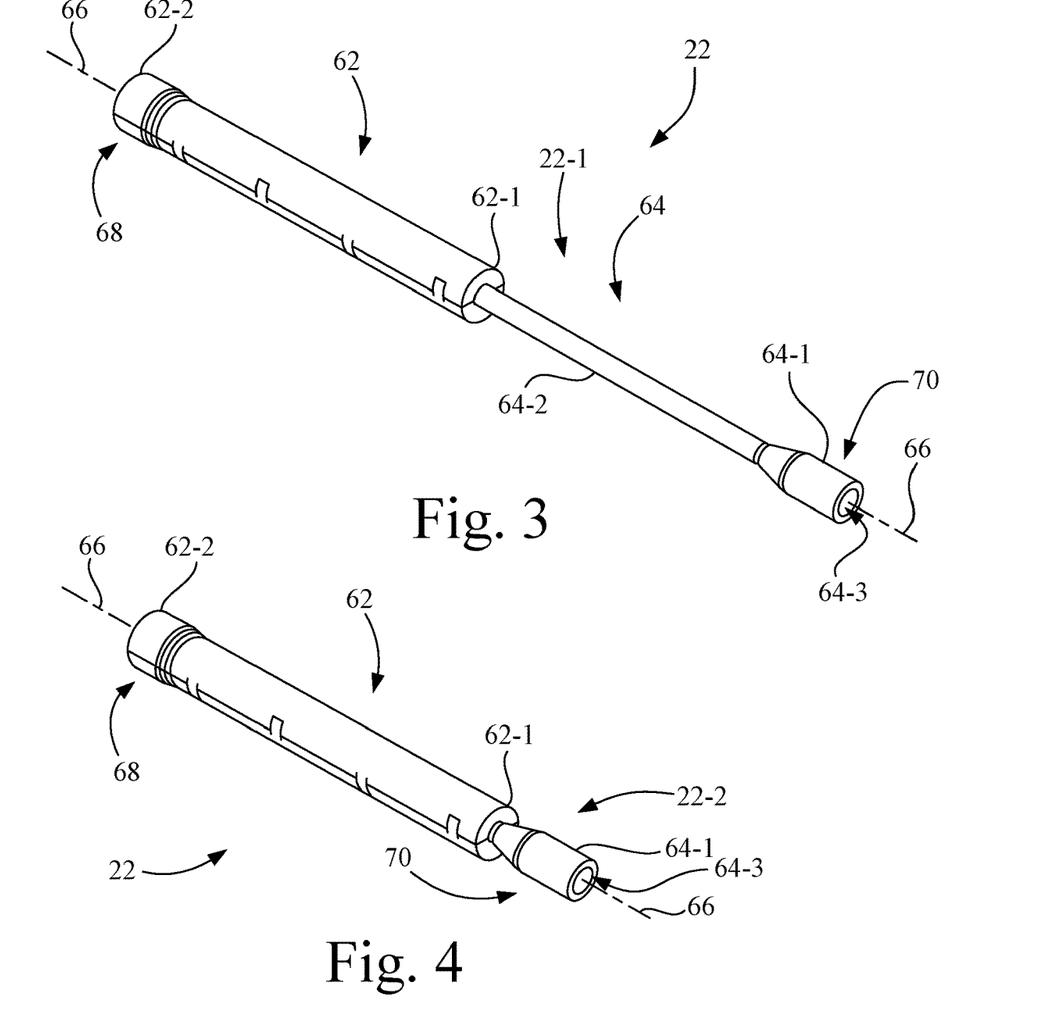
FIG. 3 is an enlarged perspective view of the adjustable interface device of FIGS. 1 and 2, with the adjustable interface device in a fully extended position.
FIG. 4 is an enlarged perspective view of the adjustable interface device of FIGS. 1 and 2, with the adjustable interface device in a fully retracted position.

Adjustable interface device 22 connects support catheter 18 to handpiece housing 34 of handpiece 16. In the present embodiment, as depicted in FIGS. 1 and 2, adjustable interface device 22 is set to an intermediate length. FIG. 3 shows adjustable interface device 22 in a fully extended position 22-1, and FIG. 4 shows adjustable interface device 22 in a fully retracted position 22-2. A length of adjustable interface device 22 is adjustable between the fully extended position 22-1 and the fully retracted position 22-2 to accommodate both crossing and atherectomy procedures.

Referring again particularly to FIGS. 1 and 2, an adjustment of a length of adjustable interface device 22 in turn adjusts a position of distal end 56-2 of catheter sheath 56 relative to the distal tip 20-2 of ultrasonic catheter 20, so as to adjust an amount of distal end portion 20-3 of ultrasonic catheter 20 that extends distally from distal end 56-2 of catheter sheath 56. For example, in the fully extended position 22-1 of adjustable interface device 22, distal end portion 20-3 of ultrasonic catheter 20 may be wholly disposed within the catheter lumen 58 of catheter sheath 56. In the fully retracted position 22-2 of adjustable interface device 22, distal tip 20-2 of ultrasonic catheter 20 will extend a maximum distance, e.g., 10 centimeters (cm), from distal end 56-2 of catheter sheath 56, such that the entirety of distal end portion 20-3 of ultrasonic catheter 20 is exposed beyond distal end 56-2 of catheter sheath 56 of support catheter 18.

Advantageously, adjustable interface device 22 provides more support to distal tip 20-2 of ultrasonic catheter 20 when extended, and adjustable interface device 22 provides more freedom to advance distal tip 20-2 of ultrasonic catheter 20 relative to support catheter 18 when retracted. Also, adjustable interface device 22 provides a general benefit of moving both support catheter 18 and ultrasonic catheter 20 as a unit during a procedure.

Referring to FIGS. 3-6, adjustable interface device 22 includes an elongate body 62 and an elongate member 64. In the present embodiment, elongate member 64 is slidably and rotationally disposed in elongate body 62. A length of adjustable interface device 22 is adjusted by longitudinally sliding elongate member 64 relative to elongate body 62. In the present embodiment, after a desired length of adjustable interface device 22 is set, then the length of adjustable interface device 22 may be locked by rotating elongate member 64 relative to elongate body 62, e.g., by a one-sixteenth to one-quarter turn of rotation of elongate member 64 relative to elongate body 62.

Elongate body 62 includes a first end 62-1, a second end 62-2, a side wall 62-3, and an interior channel 62-4. Side wall 62-3 radially surrounds interior channel 62-4. Interior channel 62-4 extends between first end 62-1 and second end 62-2 of elongate body 62. Elongate body 62 has a longitudinal axis 66 that longitudinally extends through interior channel 62-4. Side wall 62-3 is configured to define a first connector portion 68 adjacent the second end 62-2. First connector portion 68 of elongate body 62 is configured to attach to a respective one of mounting portion 38 of handpiece 20-4 of ultrasonic catheter 20 or mounting portion 60 of support catheter 18, depending on an orientation of adjustable interface device 22 relative to handpiece 20-4 of ultrasonic catheter 20 and support catheter 18.

Figure 5:
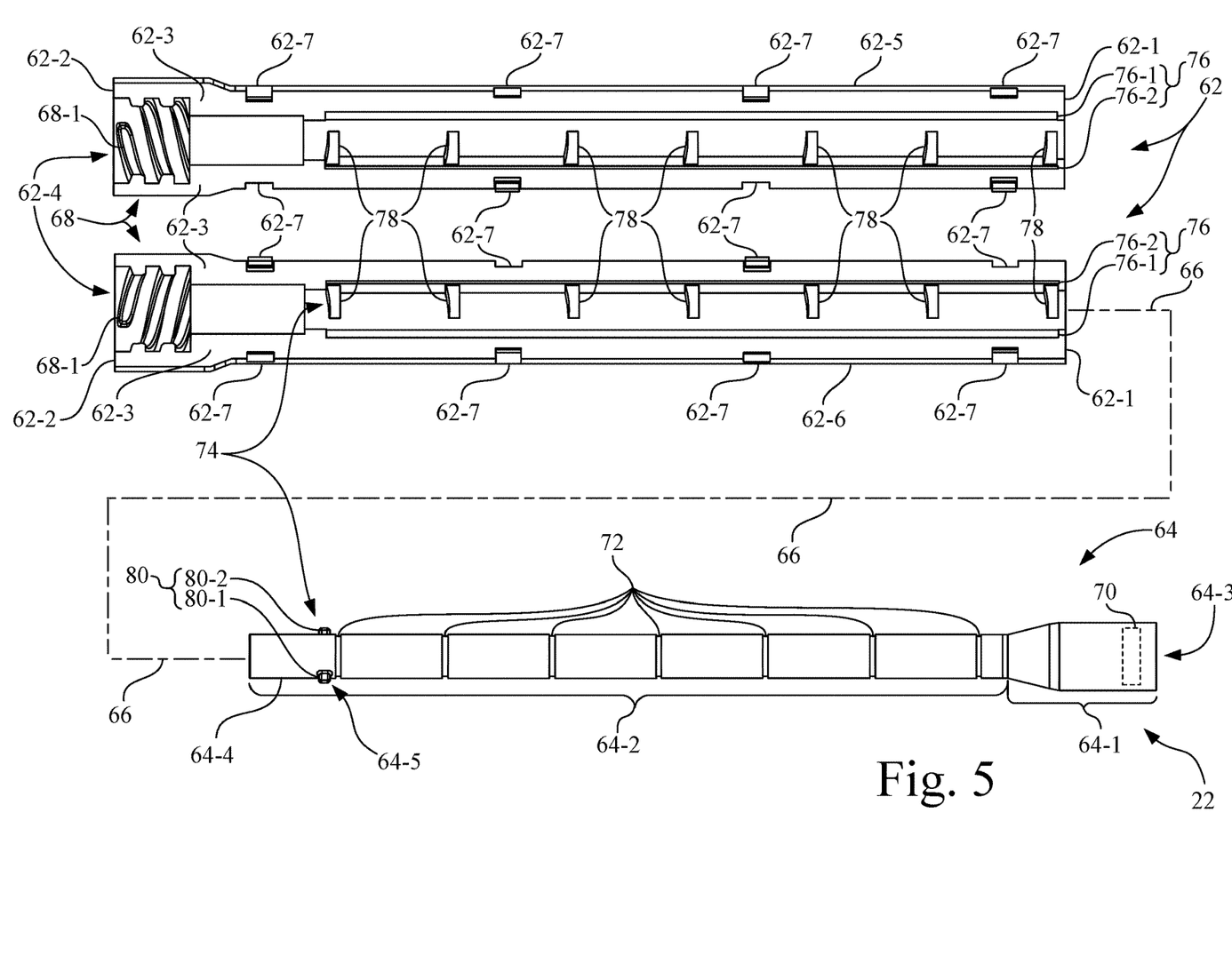
FIG. 5 is an exploded enlarged view of the adjustable interface device of FIGS. 1-4, showing an interior of an elongate body having two separable housing portions and an exterior of the elongate member, having portions that form a locking mechanism for the adjustable interface device.

As best shown in FIGS. 3-5, for ease of assembly, elongate body 62 is configured as a split housing having a pair of separable housing portions, namely, housing portion 62-5 and housing portion 62-6, wherein housing portion 62-5 and housing portion 62-6 are connected together by sets of longitudinally spaced hook-latch members 62-7.

Referring also to FIGS. 1 and 2, in the present embodiment, first connector portion 68 of elongate body 62 is configured to attach to mounting portion 60 of the support catheter 18. Also, referring to FIGS. 5 and 6, in the present embodiment, first connector portion 68 of elongate body 62 and mounting portion 60 of the support catheter 18 is configured to form a screw-type coupling, e.g., a Luer connection. For example, first connector portion 68 of elongate body 62 may be configured as a female threaded portion 68-1 and mounting portion 60 of the support catheter 18 may be configured as a male threaded portion, or vice-versa.

Figure 6:
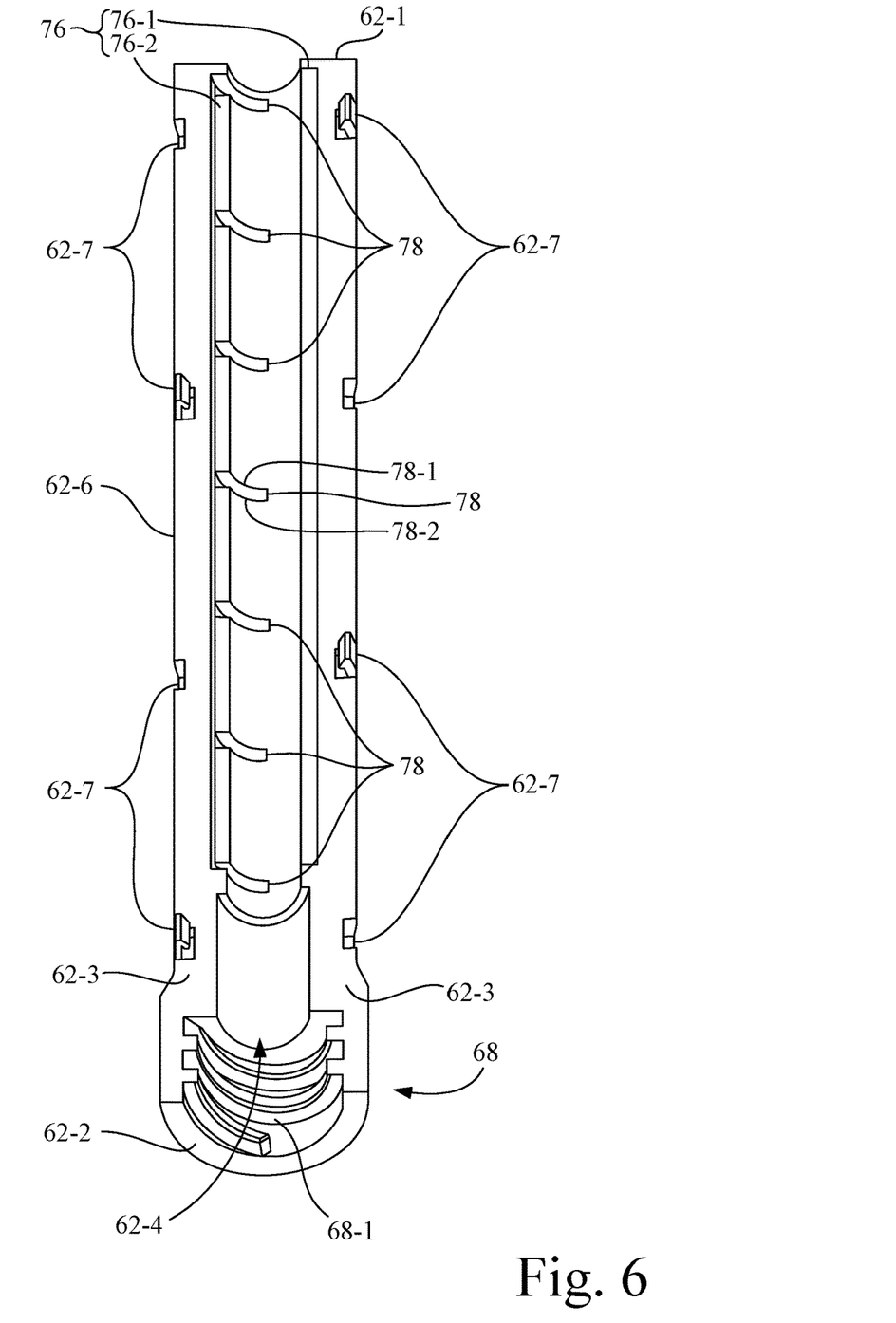
FIG. 6 is a perspective view of a housing portion of the elongate body of FIG. 5.
Figure 7:
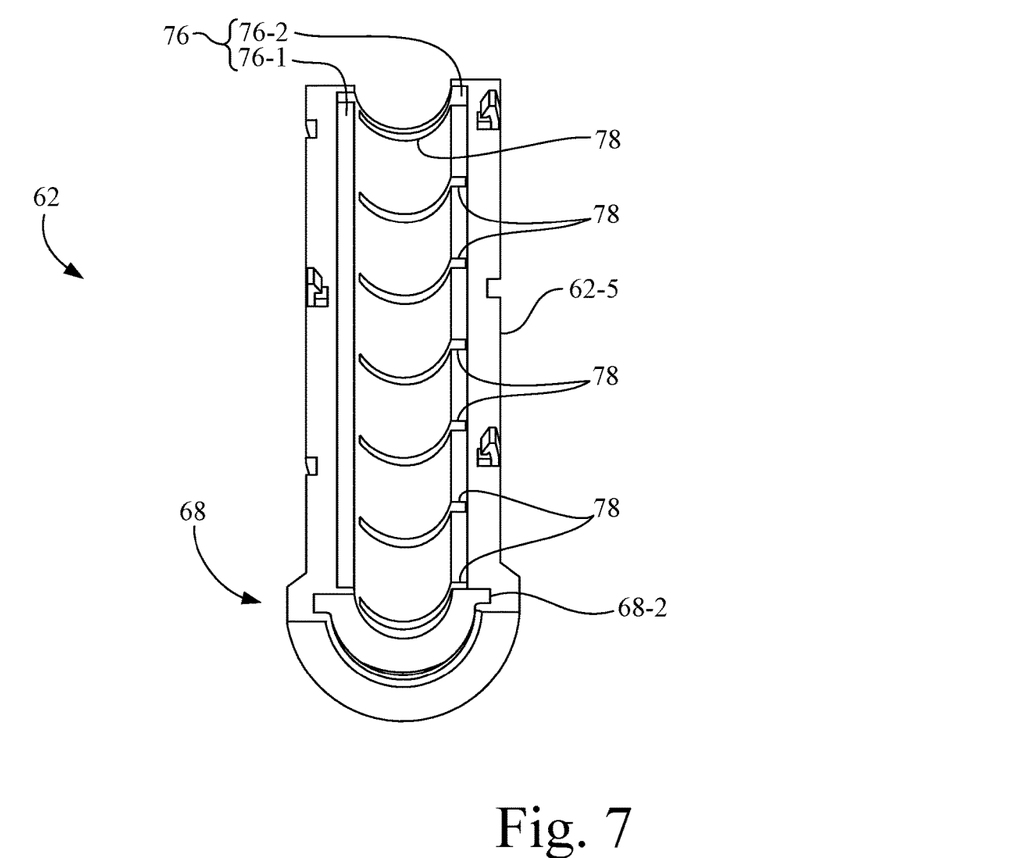
FIG. 7 is a perspective end view of a housing portion of the elongate body in accordance with another embodiment of the present invention.
Figure 8:
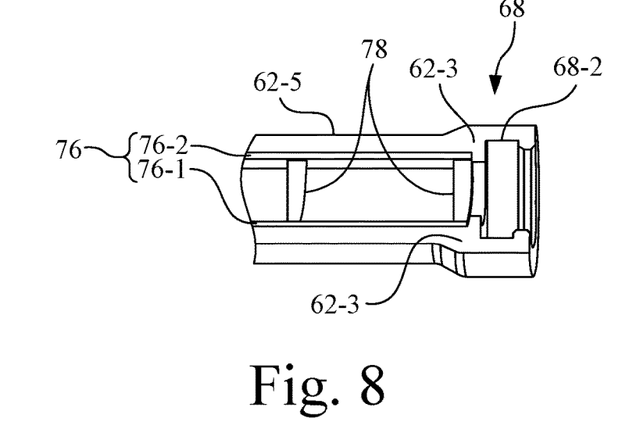
FIG. 8 is a perspective side view of a portion of the housing portion of the elongate body of FIG. 7.

FIGS. 7 and 8 show an interference, e.g., snap fit, connection as an alternative to the configuration of the embodiment depicted in FIGS. 5 and 6 that depict the screw-type coupling, e.g., a Luer connection, for connecting first connector portion 68 of elongate body 62 to mounting portion 60 of the support catheter 18. FIGS. 7 and 8 show that first connector portion 68 of elongate body 62 may be configured as a female portion having an annular recess 68-2. Mounting portion 60 of the support catheter 18 may be configured as a corresponding male portion having an annular protrusion. In operation, first connector portion 68 of elongate body 62 is moved longitudinally relative to mounting portion 60 of the support catheter 18 such that the annular recess 68-2 of first connector portion 68 of elongate body 62 is engaged by the annular protrusion of mounting portion 60 of the support catheter 18 so as to establish the snap fit (and rotatable) connection of support catheter 18 to adjustable interface device 22.

Figure 8A:
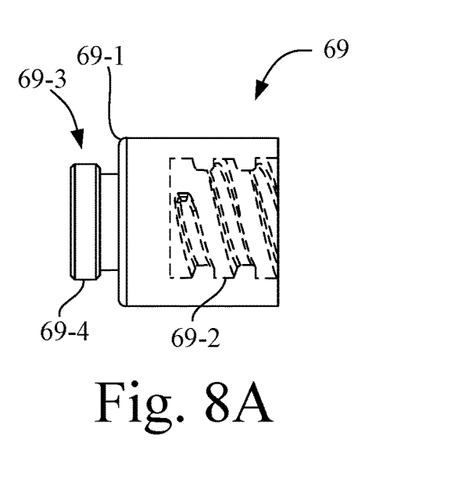
FIG. 8A is an optional adapter for use with the embodiment of FIGS. 7 and 8.

Referring to FIG. 8A, the embodiment of body 62 shown in FIGS. 7 and 8 may be converted to a screw-type connector as depicted in FIGS. 5 and 6 by the inclusion of an optional adapter 69. Adapter 69 includes a body 69-1 having a threaded end portion 69-2 and a snap-fit end portion 69-3. Snap-fit end portion 69-3 includes an annular protrusion 69-4. Annular protrusion 69-4 is configured for engagement with annular recess 68-2 of first connector portion 68 of elongate body 62. The use of adapter 69 facilitates connection of the embodiment of body 62 depicted in FIGS. 7 and 8 to a threaded connector, while facilitating full rotation of adapter 69, and therefore, also facilitating full rotation of support catheter 18.

Referring again to FIGS. 1-5, elongate member 64 includes a head end portion 64-1 and a shaft portion 64-2. Shaft portion 64-2 longitudinally extends from head end portion 64-1. Shaft portion 64-2 is located in interior channel 62-4 of the elongate body 62. Shaft portion 64-2 is configured to slidably move axially along the longitudinal axis 66 to adjust a length of the adjustable interface device 22. Head end portion 64-1 defines a second connector portion 70 that is configured to attach to a respective one of mounting portion 38 of handpiece 20-4 of ultrasonic catheter 20 and mounting portion 60 of support catheter 18, depending on an orientation of adjustable interface device 22 relative to handpiece 16 and support catheter 18.

Referring to FIGS. 1 and 2, in the present embodiment, second connector portion 70 of elongate member 64 is configured to attach to mounting portion 38 of handpiece 20-4 of ultrasonic catheter 20. Also, in the present embodiment, second connector portion 70 of elongate member 64 and mounting portion 38 of handpiece 20-4 of ultrasonic catheter 20 are configured to form an interference fit, e.g., via a snap-type coupling. For example, second connector portion 70 of elongate member 64 may be configured as a female portion having an annular recess, and mounting portion 38 of handpiece 20-4 of ultrasonic catheter 20 may be configured as a male portion having an annular protrusion, wherein second connector portion 70 of elongate member 64 is moved longitudinally relative to mounting portion 38 of handpiece 20-4 of ultrasonic catheter 20 such that the annular recess of second connector portion 70 of elongate member 64 is engaged by the annular protrusion of mounting portion 38 of handpiece 20-4 of ultrasonic catheter 20 so as to establish the snap fit connection of handpiece housing 34 to adjustable interface device 22.

Referring to FIGS. 2-5, elongate member 64 includes an elongate passage 64-3 that is in communication with the interior channel 62-4 of the elongate body 62. Elongate passage 64-3 of elongate member 64 and interior channel 62-4 of the elongate body 62 are configured to receive ultrasonic catheter 20 that is supported by the support catheter 18, wherein ultrasonic catheter 20 longitudinally extends from handpiece 16 through each of elongate passage 64-3 of elongate member 64, interior channel 62-4 of elongate body 62, and catheter lumen 58 of support catheter 18.

Optionally, as depicted in FIG. 5, shaft portion 64-2 of elongate member 64 may include a plurality of length indicators 72 longitudinally spaced along the shaft portion 64-2. The plurality of length indicators 72 are configured to indicate a distance associated with the length of adjustable interface device 22. The plurality of length indicators 72 may be, for example, in the form of etched or painted bands, and may further include numerical length indicators, if desired.

Referring to FIGS. 5 and 6, adjustable interface device 22 further includes a locking mechanism 74 configured to lock a longitudinal position of elongate member 64 relative to elongate body 62, after the length of the adjustable interface device 22 is set by a user to a desired length. In the present embodiment, locking mechanism 74 includes interior channel 62-4 of elongate body 62 and shaft portion 64-2 of the elongate member 64, as further describe below.

Interior channel 62-4 of the elongate body 62 includes a longitudinal track 76 and a plurality of arcuate tracks 78 that are formed in side wall 62-3 of elongate body 62. Longitudinal track 76 and the plurality of arcuate tracks 78 form the elongate body 62 portion of locking mechanism 74. The plurality of arcuate tracks 78 are longitudinally spaced along longitudinal track 76 and circumferentially intersect the longitudinal track 76, wherein each arcuate track of the plurality of arcuate tracks 78 is a branch extension of the longitudinal track 76. The plurality of arcuate tracks 78 of the interior channel 62-4 of elongate body 62 define a plurality of discrete increments (e.g., 2.0 cm increments) of adjustment of the length of adjustable interface device 22.

In the present embodiment, longitudinal track 76 of interior channel 62-4 of elongate body 62 includes a pair of diametrically opposed longitudinal track sections 76-1, 76-2, and each of the pair of diametrically opposed longitudinal track sections 76-1, 76-2 includes a respective plurality of complimentary arcuate track extensions formed by a respective portion of the plurality of arcuate tracks 78. Notwithstanding, it is contemplated that longitudinal track 76 may be formed by a single longitudinal track section, or multiple longitudinal track sections.

Shaft portion 64-2 of the elongate member 64 has an outer surface 64-4 and a tail end portion 64-5. Tail end portion 64-5 includes an engagement member 80 that extends radially outwardly from the outer surface 64-4. In the present embodiment, engagement member 80 includes a pair of diametrically opposed tabs 80-1, 80-2 that respectively slidably engage longitudinal track sections 76-1, 76-2. While in the present embodiment, engagement member 80 includes a pair of diametrically opposed tabs 80-1, 80-2, it is contemplated that engagement member 80 may be formed by a single tab, if desired.

With shaft portion 64-2 of the elongate member 64 positioned in interior channel 62-4 of elongate body 62, engagement member 80 engages and slides along longitudinal track 76 to facilitate longitudinal movement of elongate member 64 relative to elongate body 62 of adjustable interface device 22, so as to adjust a length of adjustable interface device 22. However, in order to lock adjustable interface device 22 to a desired length, engagement member 80 is configured to be rotatably received into a selected one of the plurality of arcuate tracks 78 of elongate body 62 so as to lock the longitudinal position of the elongate member 64 relative to the elongate body 62. For example, when elongate member 64 and elongate body 62 of adjustable interface device 22 are longitudinally positioned such that engagement member 80 is radially aligned with one of the plurality of arcuate tracks 78, then a rotation of elongate member 64 relative to elongate body 62 causes engagement member 80 to depart from longitudinal track 76 and enter the respective arcuate track of the plurality of arcuate tracks 78 of elongate body 62, thereby impeding longitudinal movement of elongate member 64 and elongate body 62.

Also, in locking mechanism 74, each arcuate track of the plurality of arcuate tracks 78 may include a pair of tapered walls 78-1, 78-2. The pair of tapered walls 78-1, 78-2 is configured such that when engagement member 80 is rotatably received into a selected one of the plurality of arcuate tracks 78, engagement member 80 of elongate member 64 is wedged between the pair of tapered walls 78-1, 78-2 so as to maintain both the rotational and longitudinal position of elongate member 64 relative to the elongate body 62, and further to impede both rotational and longitudinal movement of the elongate member 64 relative to the elongate body 62, as well as to allow for selection of length.

Figure 9:
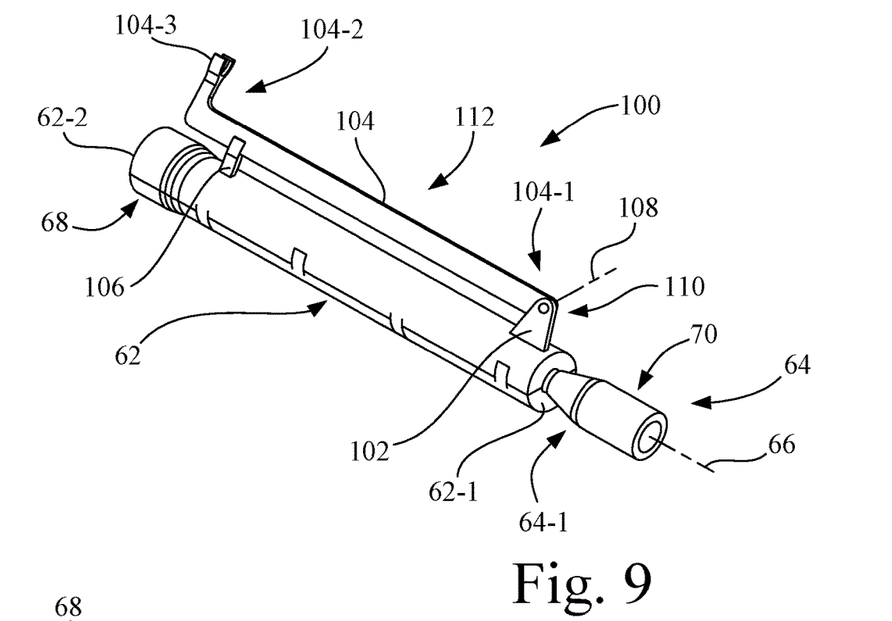
FIG. 9 is a perspective view of a locking mechanism, in accordance with another embodiment of the adjustable interface device, showing a locking lever in a stowed position.
Figure 10:
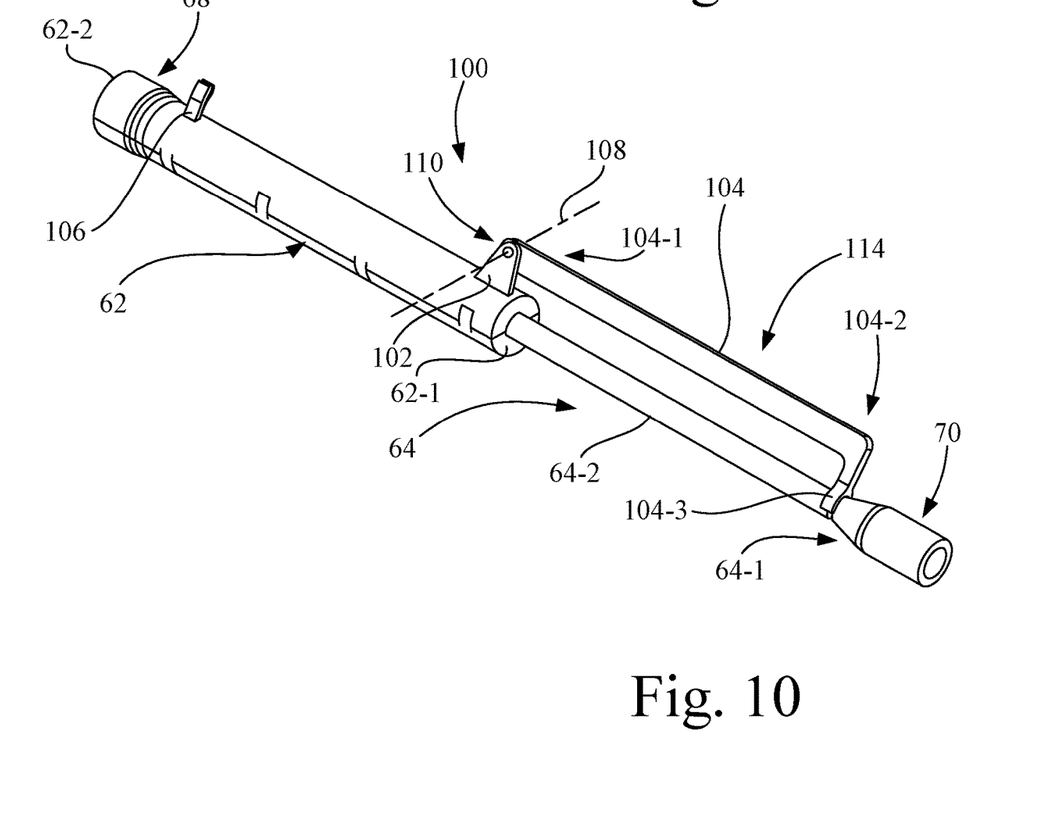
FIG. 10 is a perspective view of the locking mechanism of FIG. 9, showing the locking lever in a locking position.

FIGS. 9 and 10 depict an alternative embodiment for a locking mechanism, in the form of a locking mechanism 100. It is contemplated that locking mechanism 100 may serve as a supplemental locking mechanism to that of locking mechanism 74, or may serve as a replacement for locking mechanism 74, if desired.

Locking mechanism 100 includes a pivot member 102, locking lever 104, and a stow clip 106.

Pivot member 102 is connected to the elongate body 62. Pivot member 102 defines a pivot axis 108.

Locking lever 104 has a pivot end 104-1 and a locking end 104-2. In the present embodiment, locking end 104-2 of locking lever 104 has a U-shaped yoke 104-3 configured to clip over shaft portion 64-2 of the elongate member 64 in a snug fit, at a location adjacent, e.g., proximal, to head end portion 64-1 of elongate member 64.

Pivot end 104-1 of locking lever 104 is rotatably connected to pivot member 102 of elongate body 62 by a pivot joint 110 located at pivot axis 108. Pivot joint 110 may be, for example, a pin-hole arrangement. Locking lever 104 is configured to pivot at pivot joint 110 of pivot member 102 between a stowed position 112 as shown in FIG. 9 and a locking position 114 shown in FIG. 10.

In stowed position 112, shown in FIG. 9, locking lever 104 is disengaged from shaft portion 64-2 of elongate member 64, such that elongate member 64 may move longitudinally relative to elongate body 62. Locking lever 104 is stowed by rotating locking lever 104 about pivot axis 108 until locking lever 104 engages stow clip 106.

In the locking position 114, shown in FIG. 10, U-shaped yoke 104-3 of locking end 104-2 of locking lever 104 is engaged with, i.e., clips to, shaft portion 64-2 of the elongate member 64 adjacent to head end portion 64-1 of elongate member 64, thereby preventing a shortening of adjustable interface device 22. In operation, elongate member 64 is lengthened relative to elongate body 62, and locking lever 104 is rotated about pivot axis 108 until U-shaped yoke 104-3 of locking end 104-2 of locking lever 104 engages, i.e., clips, to shaft portion 64-2 of the elongate member 64 adjacent to head end portion 64-1 of elongate member 64.

While adjustable interface device 22 has been described above with respect to a medical system having an ultrasonic device with a particular configuration as an example of use, those skilled in the art will recognize that the adjustable interface device 22 may be adapted for use in other types of medical devices, including other types of ultrasonic devices, wherein a spacing between two medical components is to be controllably adjusted.

The following items also relate to the invention:

In one form, the invention relates to an adjustable interface device for connecting two components of a medical device. The adjustable interface device includes an elongate body and an elongate member. The elongate body has a first end, a second end, an interior channel, and a side wall that surrounds the interior channel. The interior channel is configured to extend between the first end and the second end. The elongate body may have a longitudinal axis that longitudinally extends through the interior channel. The side wall is configured to define a first connector portion adjacent the second end. The first connector portion is configured to attach to a respective one of the two components of the medical device. The elongate member has a head end portion and a shaft portion that longitudinally extends from the head end portion. The shaft portion is configured to be located at least partially in the interior channel of the elongate body. The shaft portion is configured to slidably move axially along the longitudinal axis to adjust a length of the adjustable interface device. The head end portion is configured to define a second connector portion configured to attach to the other of the two components of the medical device.

Optionally, in any of the embodiments, the elongate member may include an elongate passage that is in fluid communication with the interior channel of the elongate body, e.g., to provide a continuous passage through the elongate member and the elongate body.

Optionally, in any of the embodiments, a plurality of length indicators may be longitudinally spaced along the shaft portion. The plurality of length indicators may be configured to indicate a distance associated with the length of the adjustable interface device, such as for example, a total length of the adjustable interface device, or alternatively, a distance that the head end portion of the elongate member is displaced from the elongate body.

Optionally, in any of the embodiments, a locking mechanism may be configured to lock a longitudinal position of the elongate member relative to the elongate body after the length of the adjustable interface device, e.g., the total length from the proximal most to the distal most part of the adjustable interface device, is set to a desired length.

In any embodiment that includes the locking mechanism, the locking mechanism may include a first engagement member on the shaft portion and a second engagement member on the interior channel, the first engagement member configured to engage with the second engagement member at pre-defined intervals along the longitudinal axis of the interior channel.

In any embodiment that includes the locking mechanism, the locking mechanism may include the interior channel of the elongate body and the shaft portion of the elongate member. The interior channel of the elongate body may comprise a longitudinal track and a plurality of arcuate tracks that are formed in the side wall of the elongate body, wherein the plurality of arcuate tracks are longitudinally spaced along the longitudinal track and may circumferentially intersect the longitudinal track, and wherein each arcuate track of the plurality of arcuate tracks may be a branch extension of the longitudinal track, i.e., a track portion that branches off of the primary longitudinal track. The shaft portion of the elongate member may have an outer surface and a tail end portion, wherein the tail end portion may have an engagement member that extends radially outwardly from the outer surface. The engagement member may be configured to slide along the longitudinal track, and the engagement member may be configured to be rotatably received into a selected one of the plurality of arcuate tracks to lock the longitudinal position of the elongate member relative to the elongate body.

In the embodiment of the immediately preceding paragraph, the plurality of arcuate tracks of the interior channel of the elongate body may be configured to define a plurality of discrete increments of adjustment of the length of the adjustable interface device.

In the embodiment of the immediately preceding two paragraphs, optionally, each arcuate track of the plurality of arcuate tracks may have a pair of tapered walls, e.g., wherein the pair of tapered walls may taper in a direction away from the longitudinal track, and, wherein the pair of tapered walls may be configured such that when the engagement member is rotatably received into the selected one of the plurality of arcuate tracks, the engagement member of the elongate member is wedged between the pair of tapered walls to impede both rotational and longitudinal movement of the elongate member relative to the elongate body.

In the embodiments of the immediately preceding three paragraphs, the longitudinal track of the interior channel of the elongate body may comprise a pair of diametrically opposed longitudinal track sections, and each of the pair of diametrically opposed longitudinal track sections may include a plurality of arcuate track extensions formed by a respective portion of the plurality of arcuate tracks. The engagement member of the elongate member may comprise a pair of diametrically opposed engagement tabs, wherein the pair of diametrically opposed engagement tabs may be configured to engage the diametrically opposed longitudinal track sections.

In some embodiments, optionally, the locking mechanism may comprise a pivot member and a locking lever. The pivot member may be connected to the elongate body. The locking lever may have a pivot end and a locking end. The pivot end may be configured to be rotatably connected to the pivot member of the elongate body, the locking lever configured to pivot at the pivot member between a stowed position and a locking position, wherein in the locking position, the locking end of the locking lever may be engaged with the shaft portion of the elongate member.

In the embodiment of the immediately preceding paragraph, the locking end of the locking lever may have a U-shaped yoke shape configured to clip over the shaft portion of the elongate member in a snug fit, e.g., an interference friction fit, at a location proximal to the head end portion of the elongate member.

In any of the embodiments, the elongate body may have a connector portion that has an annular recess, and may further comprise an adapter that has a threaded end portion and a snap-fit end portion. The snap-fit end portion may have an annular protrusion that is configured for engagement with the annular recess of the connector portion of the elongate body.

In another form, the invention relates to as ultrasonic device that may include a handpiece, a support catheter, and an adjustable interface device according to any of the embodiments described above.

The handpiece may include a handpiece housing, and an ultrasonic catheter connected to the handpiece housing. The handpiece housing may be configured with an outer shape and size to facilitate being grasped by an operator. The ultrasonic catheter may have a first mounting portion. The support catheter may have a catheter body and a catheter sheath that may be connected to the catheter body. The catheter body may have a second mounting portion. The catheter sheath has a distal end. The adjustable interface device may be configured to connect the support catheter to the ultrasonic catheter. The adjustable interface device may comprise an elongate body and an elongate member. The elongate body may have a first end, a second end, an interior channel, and a side wall that surrounds the interior channel. The interior channel may be configured to extend between the first end and the second end. The elongate body may have a longitudinal axis that longitudinally extends through the interior channel. The side wall may be configured to define a first connector portion adjacent the second end. The first connector portion may be configured to attach to a respective one of the first mounting portion of the ultrasonic catheter and the second mounting portion of the support catheter. The elongate member may have a head end portion and a shaft portion that longitudinally extends from the head end portion. The shaft portion may be located at least partially in the interior channel of the elongate body. The shaft portion may be configured to slidably move axially along the longitudinal axis to adjust a length of the adjustable interface device. The head end portion may be configured to define a second connector portion configured to attach to the other of the first mounting portion of the ultrasonic catheter and the second mounting portion of the support catheter.

Optionally, in any of the embodiments, the elongate member optionally may include an elongate passage that is in communication with the interior channel of the elongate body. In the ultrasonic device embodiment, the elongate passage and the interior channel may be configured to receive an ultrasonic transmission member that may be supported by the support catheter.

Optionally, in any of the embodiments, a plurality of length indicators longitudinally may be spaced along the shaft portion, wherein the plurality of length indicators may be configured to indicate a distance associated with the length of the adjustable interface device.

Optionally, in any of the embodiments, a locking mechanism may be configured to lock a longitudinal position of the elongate member relative to the elongate body after the length of the adjustable interface device is set to a desired length.

In any embodiment that includes the locking mechanism, the locking mechanism may include the interior channel of the elongate body and the shaft portion of the elongate member. The interior channel of the elongate body may comprise a longitudinal track and a plurality of arcuate tracks that are formed in the side wall of the elongate body, wherein the plurality of arcuate tracks may be longitudinally spaced along the longitudinal track and circumferentially intersect the longitudinal track, and wherein each arcuate track of the plurality of arcuate tracks may be a branch extension of the longitudinal track. The shaft portion of the elongate member may have an outer surface and a tail end portion. The tail end portion may have an engagement member that extends radially outwardly from the outer surface. The engagement member may be configured to slide along the longitudinal track. The engagement member may be configured to be rotatably received into a selected one of the plurality of arcuate tracks to lock the longitudinal position of the elongate member relative to the elongate body.

In the embodiment of the immediately preceding paragraph, the plurality of arcuate tracks of the interior channel of the elongate body may be configured to define a plurality of discrete increments of adjustment of the length of the adjustable interface device.

In the embodiment of the immediately preceding two paragraphs, optionally, each arcuate track of the plurality of arcuate tracks may have a pair of tapered walls, wherein the pair of tapered walls may be configured such that when the engagement member is rotatably received into the selected one of the plurality of arcuate tracks, the engagement member of the elongate member is wedged between the pair of tapered walls to impede both rotational and longitudinal movement of the elongate member relative to the elongate body.

In the embodiment of the immediately preceding three paragraphs, optionally, the longitudinal track of the interior channel of the elongate body may comprise a pair of diametrically opposed longitudinal track sections. Each of the pair of diametrically opposed longitudinal track sections may include a plurality of arcuate track extensions formed by a respective portion of the plurality of arcuate tracks. The engagement member of the elongate member may comprise a pair of diametrically opposed engagement tabs, wherein the pair of diametrically opposed engagement tabs are configured to engage the diametrically opposed longitudinal track sections.

In some embodiments, optionally, the locking mechanism may comprise a pivot member and a locking lever. The pivot member may be connected to the elongate body. The locking lever may have a pivot end and a locking end. The pivot end may be configured to be rotatably connected to the pivot member of the elongate body. The locking lever may be configured to pivot at the pivot member between a stowed position and a locking position, wherein in the locking position, the locking end of the locking lever may be engaged with the shaft portion of the elongate member.

In the embodiment of the immediately preceding paragraph, the locking end of the locking lever may have a U-shaped yoke shape configured to clip over the shaft portion of the elongate member in a snug fit, at a location proximal to the head end portion of the elongate member.

For definitional purposes, unless specified, the terms "connected" or "attached" are intended to embrace any operationally functional connection, whether direct or indirect.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An adjustable interface device for connecting two components of a medical device, comprising:
    an elongate body having a first end, a second end, an interior channel, and a side wall that surrounds the interior channel, the interior channel configured to extend between the first end and the second end, the elongate body having a longitudinal axis that longitudinally extends through the interior channel, the side wall configured to define a first connector portion adjacent the second end, the first connector portion having an annular recess, the first connector portion configured to attach to a respective one of the two components of the medical device;
    an elongate member having a head end portion and a shaft portion that longitudinally extends from the head end portion, the shaft portion being located at least partially in the interior channel of the elongate body, the shaft portion configured to slidably move axially along the longitudinal axis to adjust a length of the adjustable interface device, the head end portion defining a second connector portion configured to attach to the other of the two components of the medical device; and
    an adapter having a threaded end portion and a snap-fit end portion, the snap-fit end portion having an annular protrusion configured for engagement with the annular recess of the first connector portion of the elongate body.

2. The adjustable interface device according to claim 1, wherein the elongate member includes an elongate passage that is in communication with the interior channel of the elongate body.

3. The adjustable interface device according to claim 1, comprising a plurality of length indicators longitudinally spaced along the shaft portion, the plurality of length indicators configured to indicate a distance associated with the length of the adjustable interface device.

4. The adjustable interface device according to claim 1, comprising a locking mechanism configured to lock a longitudinal position of the elongate member relative to the elongate body after the length of the adjustable interface device is set to a desired length.

5. The adjustable interface device according to claim 4, wherein the locking mechanism includes a first engagement member on the shaft portion and a second engagement member on the interior channel, the first engagement member configured to engage with the second engagement member at pre-defined intervals along the longitudinal axis of the interior channel.

6. The adjustable interface device according to claim 4, wherein the locking mechanism includes the interior channel of the elongate body and the shaft portion of the elongate member, and wherein:
    the interior channel of the elongate body comprises a longitudinal track and a plurality of arcuate tracks that are formed in the side wall of the elongate body, wherein the plurality of arcuate tracks are longitudinally spaced along the longitudinal track and circumferentially intersect the longitudinal track, wherein each arcuate track of the plurality of arcuate tracks is a branch extension of the longitudinal track; and
    the shaft portion of the elongate member has an outer surface and a tail end portion, the tail end portion having an engagement member that extends radially outwardly from the outer surface, the engagement member configured to slide along the longitudinal track, and the engagement member configured to be rotatably received into a selected one of the plurality of arcuate tracks to lock the longitudinal position of the elongate member relative to the elongate body.

7. The adjustable interface device according to claim 6, wherein the plurality of arcuate tracks of the interior channel of the elongate body define a plurality of discrete increments of adjustment of the length of the adjustable interface device.

8. The adjustable interface device according to claim 6, wherein each arcuate track of the plurality of arcuate tracks has a pair of tapered walls, wherein the pair of tapered walls is configured such that when the engagement member is rotatably received into the selected one of the plurality of arcuate tracks, the engagement member of the elongate member is wedged between the pair of tapered walls to impede both rotational and longitudinal movement of the elongate member relative to the elongate body.

9. The adjustable interface device according to claim 6, wherein:
    the longitudinal track of the interior channel of the elongate body comprises a pair of diametrically opposed longitudinal track sections, and each of the pair of diametrically opposed longitudinal track sections includes a plurality of arcuate track extensions formed by a respective portion of the plurality of arcuate tracks; and
    the engagement member of the elongate member comprises a pair of diametrically opposed engagement tabs, wherein the pair of diametrically opposed engagement tabs engage the diametrically opposed longitudinal track sections.

10. The adjustable interface device according to claim 4, wherein the locking mechanism comprises:
    a pivot member connected to the elongate body,
    a locking lever having a pivot end and a locking end, the pivot end configured to be rotatably connected to the pivot member of the elongate body, the locking lever configured to pivot at the pivot member between a stowed position and a locking position, wherein in the locking position, the locking end of the locking lever is engaged with the shaft portion of the elongate member.

11. The adjustable interface device according to claim 10, wherein the locking end of the locking lever has a U-shaped yoke configured to clip over the shaft portion of the elongate member in a snug fit, at a location proximal to the head end portion of the elongate member.

12. An ultrasonic device, comprising:
a handpiece that includes a handpiece housing, and an ultrasonic catheter connected to the handpiece housing, the handpiece housing configured with an outer shape and size to facilitate being grasped by an operator, the ultrasonic catheter having a first mounting portion;
a support catheter having a catheter body and a catheter sheath connected to the catheter body, the catheter body having a second mounting portion, the catheter sheath having a distal end; and
an adjustable interface device configured to connect the support catheter to the ultrasonic catheter, adjustable interface device comprising:
an elongate body having a first end, a second end, an interior channel, and a side wall that surrounds the interior channel, the interior channel configured to extend between the first end and the second end, the elongate body having a longitudinal axis that longitudinally extends through the interior channel, the side wall configured to define a first connector portion adjacent the second end, the first connector portion having an annular recess, the first connector portion configured to attach to a respective one of the first mounting portion of the ultrasonic catheter and the second mounting portion of the support catheter;
an elongate member having a head end portion and a shaft portion that longitudinally extends from the head end portion, the shaft portion being located at least partially in the interior channel of the elongate body, the shaft portion configured to slidably move axially along the longitudinal axis to adjust a length of the adjustable interface device, the head end portion defining a second connector portion configured to attach to the other of the first mounting portion of the ultrasonic catheter and the second mounting portion of the support catheter; and
an adapter having a threaded end portion and a snap-fit end portion, the snap-fit end portion having an annular protrusion configured for engagement with the annular recess of the first connector portion of the elongate body.

13. The ultrasonic device according to claim 12, wherein the elongate member includes an elongate passage that is in communication with the interior channel of the elongate body, the elongate passage and the interior channel configured to receive an ultrasonic transmission member that is supported by the support catheter.

14. The ultrasonic device according to claim 12, comprising a plurality of length indicators longitudinally spaced along the shaft portion, the plurality of length indicators configured to indicate a distance associated with the length of the adjustable interface device.

15. The ultrasonic device according to claim 12, comprising a locking mechanism configured to lock a longitudinal position of the elongate member relative to the elongate body after the length of the adjustable interface device is set to a desired length.

16. The ultrasonic device according to claim 15, wherein the locking mechanism includes the interior channel of the elongate body and the shaft portion of the elongate member, and wherein:
the interior channel of the elongate body comprises a longitudinal track and a plurality of arcuate tracks that are formed in the side wall of the elongate body, wherein the plurality of arcuate tracks are longitudinally spaced along the longitudinal track and circumferentially intersect the longitudinal track, wherein each arcuate track of the plurality of arcuate tracks is a branch extension of the longitudinal track; and
the shaft portion of the elongate member has an outer surface and a tail end portion, the tail end portion having an engagement member that extends radially outwardly from the outer surface, the engagement member configured to slide along the longitudinal track, and the engagement member configured to be rotatably received into a selected one of the plurality of arcuate tracks to lock the longitudinal position of the elongate member relative to the elongate body.

17. The ultrasonic device according to claim 16, wherein the plurality of arcuate tracks of the interior channel of the elongate body define a plurality of discrete increments of adjustment of the length of the adjustable interface device.

18. The ultrasonic device according to claim 16, wherein each arcuate track of the plurality of arcuate tracks has a pair of tapered walls, wherein the pair of tapered walls is configured such that when the engagement member is rotatably received into the selected one of the plurality of arcuate tracks, the engagement member of the elongate member is wedged between the pair of tapered walls to impede both rotational and longitudinal movement of the elongate member relative to the elongate body.

19. The ultrasonic device according to claim 16 wherein:
the longitudinal track of the interior channel of the elongate body comprises a pair of diametrically opposed longitudinal track sections, and each of the pair of diametrically opposed longitudinal track sections includes a plurality of arcuate track extensions formed by a respective portion of the plurality of arcuate tracks; and
the engagement member of the elongate member comprises a pair of diametrically opposed engagement tabs, wherein the pair of diametrically opposed engagement tabs engage the diametrically opposed longitudinal track sections.

20. The ultrasonic device according to claim 15, wherein the locking mechanism comprises:
a pivot member connected to the elongate body,
a locking lever having a pivot end and a locking end, the pivot end configured to be rotatably connected to the pivot member of the elongate body, the locking lever configured to pivot at the pivot member between a stowed position and a locking position, wherein in the locking position, the locking end of the locking lever is engaged with the shaft portion of the elongate member.

21. The ultrasonic device according to claim 20, wherein the locking end of the locking lever has a U-shaped yoke configured to clip over the shaft portion of the elongate member in a snug fit, at a location proximal to the head end portion of the elongate member.

* * * * *